(12) United States Patent
Tourniaire

(10) Patent No.: US 8,268,984 B2
(45) Date of Patent: Sep. 18, 2012

(54) **DETECTION OF *SALMONELLA* BY REAL-TIME MULTIPLEX PCR**

(75) Inventor: Jean-Philippe Tourniaire, Saint Cloud (FR)

(73) Assignee: Bio-Rad Innovations, Marnes la Coquette (FR)

( * ) Notice: Subject to any disclaimer, the term of this patent is extended or adjusted under 35 U.S.C. 154(b) by 285 days.

(21) Appl. No.: 12/438,992

(22) PCT Filed: Sep. 3, 2007

(86) PCT No.: PCT/EP2007/007669
§ 371 (c)(1),
(2), (4) Date: Feb. 26, 2009

(87) PCT Pub. No.: WO2008/025570
PCT Pub. Date: Mar. 6, 2008

(65) Prior Publication Data
US 2009/0298076 A1    Dec. 3, 2009

(30) Foreign Application Priority Data
Sep. 1, 2006 (EP) .................................. 06291388

(51) Int. Cl.
*C07H 21/04* (2006.01)
*C12P 19/34* (2006.01)
(52) U.S. Cl. .................. 536/24.33; 435/6.12; 536/24.32
(58) Field of Classification Search ........................ None
See application file for complete search history.

(56) References Cited

U.S. PATENT DOCUMENTS
5,824,795 A * 10/1998 Popoff et al. ................ 536/24.3
6,080,545 A    6/2000 Popoff et al.

OTHER PUBLICATIONS

Rychlik and Rhoads (1989) A computer program for choosing optimal oligonucleotides for filter hybridization, sequencing and in vitro amplification of DNA Nucleic acids research vol. 17 No. 21 pp. 8543-8550.*
Wong and Medrano (2005) Biotechniques vol. 39 No. 1 pp. 75-85.*
BLAST search Results Nov. 2011.*
Touron Aurelie et al., "Detection of *Salmonella* in environmental water and sediment by a nested-multiplex polymerase chain reaction assay", Research in Microbiology, vol. 156, No. 4, May 2005, pp. 541-553, XP002426758.
Wang et al., "Enrichment and DNA extraction protocols for the simultaneous detection of *Salmonella* and Listeria monocytogenes in raw sausage meat with multiplex real-time PCR", Journal of Food Rpotection, Des Moines, IO, US, vol. 67, No. 1, 2004, pp. 189-192, XP008033375.
Desbouchages L. et al., "Rapid detection by real-time PCR of virulence factor of enteric *Salmonella*." Abstracts of the General Meeting of the American Society for Microbiology, vol. 104, 2003, pp. C-368 URL, XP009081205.
Markoulatos P. et al., "Multiplex polymerase chain reaction: A practical approach", Journal of Clinical Laboratory Analysis 2002 United States, vol. 16, No. 1, 2002, pp. 47-51, XP002426759.
Miras I. et al., "Nucleotide sequence of iagA and iagB genes involved in invasion of HeLa cells by *Salmonella enterica* subsp. enterica ser. Typhi", Research in Microbiology, vol. 146, No. 1, 1995, pp. 17-20, XP002426760.
May, Alex C.W., "Percent sequence identity: The need to be explicit", Structure, vol. 12, May 2004, pp. 737-738.

* cited by examiner

*Primary Examiner* — Samuel Woolwine
*Assistant Examiner* — Suchira Pande
(74) *Attorney, Agent, or Firm* — Birch, Stewart, Kolasch & Birch, LLP

(57) ABSTRACT

The invention relates to the detection of *Salmonella* by nucleic acid amplification. The invention provides primer and probe oligonucleotides that can be used in multiplex to detect *Salmonella* in real-time amplification. The oligonucleotides of the invention detect all group I serovars, and have an increased *Salmonella* detection range: they enable to cover the seven *Salmonella* groups. They also have an increased sensitivity, without loss in specificity.

18 Claims, 3 Drawing Sheets

CIP 82.29

CIP 82.30

CIP 82.31

CIP 82.32

CIP 82.33

CIP 102501

DETECTION OF *SALMONELLA* BY REAL-TIME MULTIPLEX PCR

FIELD OF THE INVENTION

The invention relates to the detection of the bacteria of the genus *Salmonella*. The invention provides oligonucleotides that enable the detection of *Salmonella* by nucleic acid hybridization, notably by nucleic acid amplification, more particularly, by PCR, advantageously by multiplex amplification (e.g., multiplex PCR), very advantageously, by real-time multiplex amplification (e.g., real-time multiplex PCR).

BACKGROUND OF THE INVENTION

*Salmonella* is a genus of bacteria that are causative of severe infections, notably of food or beverage toxi-infections, leading to bacterial enteric illness in both humans and animals, more particularly to salmonellosis, which include gastro-enteritis, as well as typhoid and para-typhoid fevers.

*S. enterica* subsp. *enterica* serovar *Typhi* and some *S. enterica* subsp. *enterica* serovar Paratyphi strains are the causative agents of typhoid fever.

There are currently more than 2,500 *Salmonella* serovars. Millions of human cases are reported worldwide every year, and the diseases result in thousands of deaths.

In recent years, problems related to *Salmonella* have increased significantly, both in terms of incidence and severity of cases of human salmonellosis.

Prior art method for the detection of *Salmonella* in food products comprises microbiology methods, which are described in European Standard ISO EN 6579:2002. Such food testing methods comprise lengthy culture steps, namely:

i. a pre-enrichment step on a non-selective liquid medium, which comprises the inoculation of a sample of the material to be assayed for, in buffered peptone water, and the incubation of the inoculated medium at 37° C. for 18±2 hours, ii. a selective pre-enrichment step, which is performed on two selective liquid media, by:
  a. inoculating 0.1 mL of the incubated medium in 10 mL of RVS broth (Rappaport Vassiliadis single component enrichment broth), and incubating at 41.5±1° C. for 24±3 hours, and
  b. inoculating 1 mL of the incubated medium in 10 mL of MKKTTn broth (Muller Kauffman Tetrathionate-novobiocine broth), and incubating at 37±1° C. for 24±3 hours, iii. an isolation step, which comprises inoculating an aliquot of each of the two above-mentioned liquid cultures, in two selective solid media, namely one XLD medium and another medium enabling the growth of lactose-positive *Salmonella* strains, and incubating these solid media at 37±1° C. for 24±3 hours, iv. an identification step, and v. a confirmation step, which comprises an agar culture at 37±1° C. for 24±3 hours, as well as a biochemical and a serological confirmation.

This method is the Standard International ISO method for the detection of *Salmonella*.

Other methods have been developed, which uses molecular biology, more particularly nucleic acid hybridization.

Illustrative of such methods are the method described in EP 0 721 989 B1 in the names of INSTITUT PASTEUR and INSERM (U.S. Pat. No. 5,824,795; U.S. Pat. No. 6,080,545), wherein oligonucleotides are disclosed to be useful as primers and probes. More particularly, oligonucleotides lag3 and lag6 are disclosed, wherein lag6 can be used as a primer within a primer pair formed with another oligonucleotide, namely lag5, and wherein lag3 can be used as a revealing probe.

The present application relates to an improved set of primers and probe, and to an improved method of *Salmonella* detection, which do not have the drawbacks of prior art techniques, and which further show unexpected effects and advantages.

The present application notably provides a set of primers and a probe, which can be used in multiplex in the same tube in real-time amplification, and which thereby enables to cover seven *Salmonella* groups in a single-tube operation. The set of primers and probe of the invention has the further advantage of having an increased sensitivity, without any loss in specificity.

SUMMARY OF THE INVENTION

The invention relates to the detection of the bacteria of the genus *Salmonella*. The invention provides oligonucleotides that enable the detection of *Salmonella* by nucleic acid hybridization, notably by nucleic acid amplification, more particularly, by PCR, advantageously by multiplex amplification (e.g., multiplex PCR), very advantageously, by real-time multiplex amplification (e.g., real-time multiplex PCR).

The oligonucleotides of the invention have the special advantage of enabling to perform real-time multiplex amplification with increased sensitivity, and wider *Salmonella* detection range, without loss in specificity.

The oligonucleotides of the invention notably enable to cover the seven *Salmonella* groups (groups I, II, IIIa, IIIb, IV, V, VI) in real-time multiplex PCR. They further enable to cover all group I serovars.

The detection sensitivity reaches a previously-unattained detection threshold (accurate sensitivity at dilutions of $10^{-7}$ or $10^{-8}$ for most strains), without loss in specificity.

Illustrative results are shown in the "Examples" section below, that show that the oligonucleotides of the invention have a wide *Salmonella* inclusivity and a sharp sensitivity, even when they are used in real-time multiplex amplification.

For each strain, three oligonucleotide sets are compared:
  SET 2: primers of SEQ ID NO: 1, 2, 3 and 4; and probe of SEQ ID NO:8;
  SET 3: primers of SEQ ID NO: 1, 2, 3 and 4; and probe of SEQ ID NO:6;
  SET 4: primers of SEQ ID NO: 1, 2, 3 and 4; and probes of SEQ ID NO:6 and of SEQ ID NO: 8.

Figure 1:
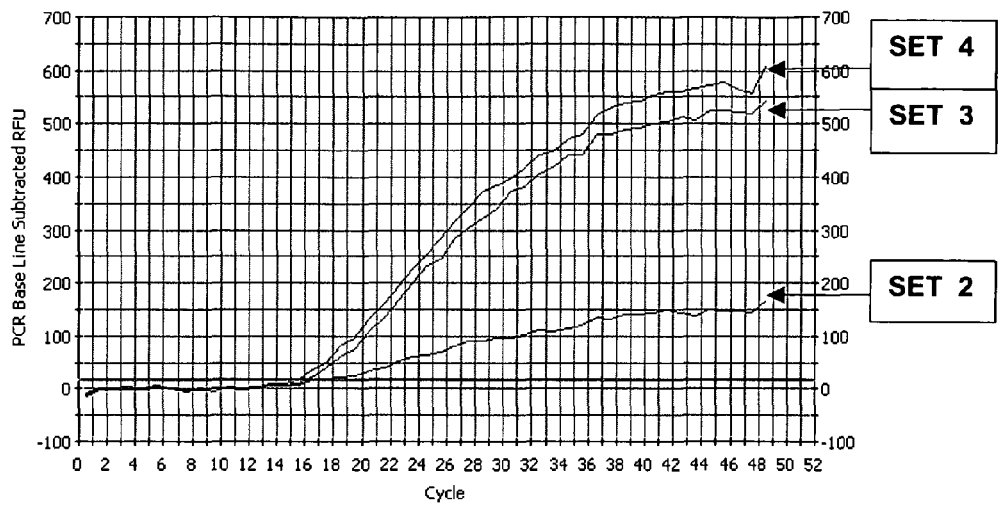
FIGS. 1-6 illustrate the curves that are obtained by submitting the nucleic acids of a reference *Salmonella* strain to real-time PCR using an oligonucleotide set of the invention (multiplex of primers and probe(s)).
Figure 2:
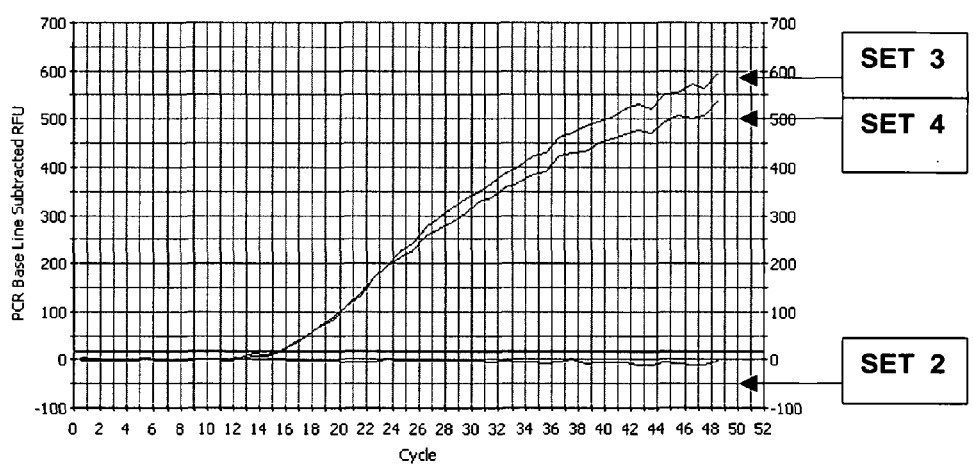
Figure 3:
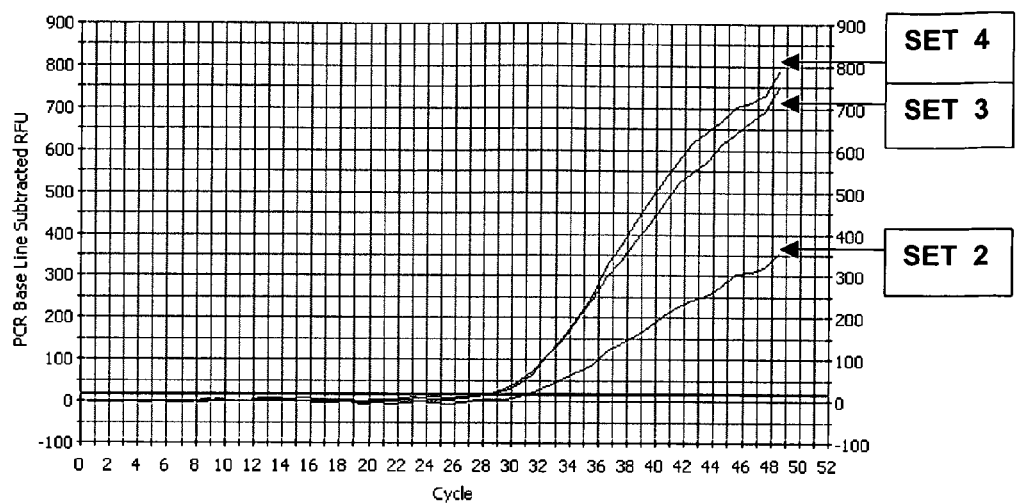
Figure 4:
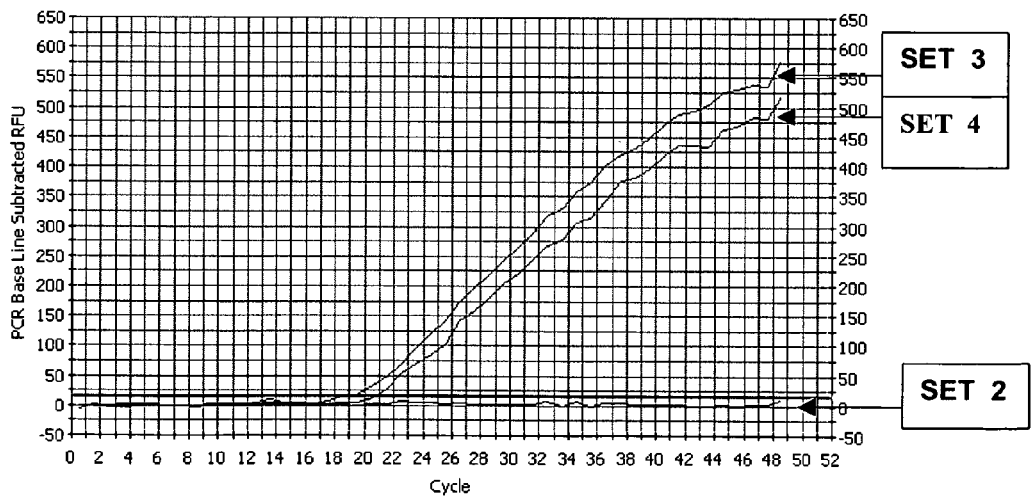
Figure 5:
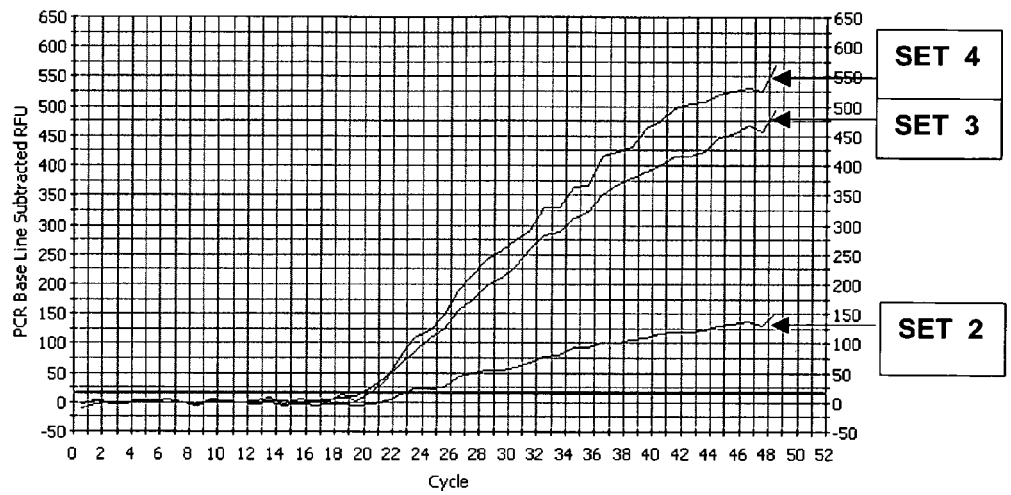
Figure 6:
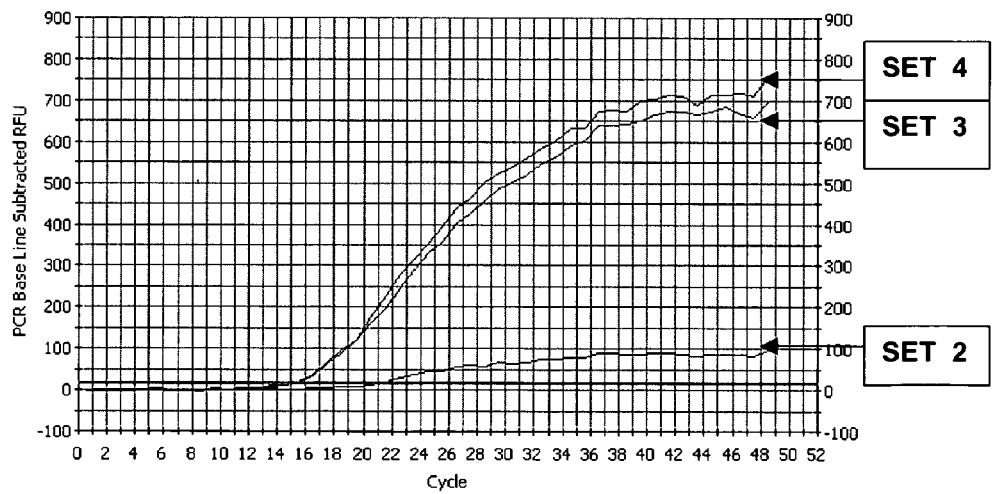

FIG. 1: *S. enterica* subsp. *salamae* (group II) strain CIP 82.29;

FIG. 2: *S. enterica* subsp. *arizonae* (group IIIa) strain CIP 82.30;

FIG. 3: *S. enterica* subsp. *diarizonae* (group IIIb) strain CIP 82.31;

FIG. 4: *S. enterica* subsp. *houtanae* (group IV) strain CIP 82.32;

FIG. 5: *S. bongori* (group V) strain CIP 82.33;

FIG. 6: *S. enterica* subsp. *indica* (group VI) strain CIP 102501.

DETAILED DESCRIPTION

In the present application, the *Salmonella* nomenclature is that of Le Minor and Popoff, 1987 (Le Minor L and Popoff M Y, "Request for an opinion. Designation of *Salmonella enterica* sp. nov., nom. rev., as the type and only species of the genus *Salmonella*", Int. J. Syst. Bacteriol. 1987; 37: 465-468).

The genus *Salmonella* is divided into two species, *S. enterica* and *S. bongori*. *S. enterica* is divided into six groups (groups I, II, IIIa, IIIb, IV, and VI). *S. bongori* contains one group (group V); see table 1 below.

TABLE 1

| Name | Accession number of the reference strains | Group |
|---|---|---|
| S. enterica subsp. enterica | CIP 60.62 (serovar Typhimurium) | I |
| S. enterica subsp. salamae | CIP 82.29 | II |
| S. enterica subsp. arizonae | CIP 82.30 | IIIa |
| S. enterica subsp. diarizonae | CIP 82.31 | IIIb |
| S. enterica subsp. houtanae | CIP 82.32 | IV |
| S. bongori | CIP 82.33 | V |
| S. enterica subsp. indica | CIP 102501 | VI |

Each of these strains is available from the C.N.C.M. (Collection Nationale de Cultures de Microorganismes; Institut Pasteur; 25, rue du Docteur Roux; F-75724 Paris Cedex 15; France). The CIP number is the C.N.C.M. strain deposit number.

A detailed description of the nomenclature and taxonomy of the genus *Salmonella*, as well as alternative strain sources (ATCC, DSM, etc.), can further be found in Tindall et al. 2005 (International Journal of Systemic and Evolutionary Microbiology, 2005, 55: 521-524), and Popoff et al. 2000 (Supplement 1998 (no. 42) to the Kauffmann-White scheme Res. Microbiol. 2000; 151: 63-65).

In the present application, reference is made to the following SEQ ID oligonucleotides:

The invention relates to a set of oligonucleotides, more particularly to this set, for use as a primer set, still more particularly for use as a primer set in the amplification of at least one nucleic acid from a *Salmonella* bacterium, advantageously, for use as a primer set that enables to cover the seven *Salmonella* groups in a single-tube experiment.

Indeed, said oligonucleotides are especially adapted to be used in multiplex in the same tube to amplify at least one nucleic acid from the nucleic acid material of *Salmonella* strains belonging to groups I, II, IIIa, IIIb, IV, V and VI. They can be used in multiplex in the same tube, without loss of specificity. Advantageously, when they are used in multiplex, the sensitivity of the amplification reaction is increased.

They also enable to amplify all group I serovars, and notably the following *S. enterica* subsp. *enterica* serovars: *S.* Typhimurium, *S.* Typhi, *S.* Paratyphi, *S.* Virchow, *S.* Hadar, *S.* Enteritidis, *S.* Anatum, *S.* Senftenberg, *S.* Cerro, *S.* Poona, *S.* Grumpensis, *S.* Dalhem, *S.* Kentucky, *S.* Lomita, *S.* Kirkee, *S.* Bredeney, *S.* Carrau, *S.* Aberdeen, *S.* Tenessee.

Said set comprises at least three oligonucleotides selected from:
  at least one oligonucleotide of sub-set A, wherein said sub-set A consists of the oligonucleotide of SEQ ID NO: 2, the conservative fragments thereof, and the conservative variants of said oligonucleotide and of said fragments, said conservative variants having a sequence identity of at least 85% with said oligonucleotide and/or with at least one of said fragments, over the entire length of said oligonucleotide and/or fragment, respectively, and
  at least one oligonucleotide of sub-set B, wherein said sub-set B consists of the oligonucleotide of SEQ ID NO: 4, the conservative fragments thereof, and the conservative variants of said oligonucleotide and of said fragments, said conservative variants having a sequence identity of at least 85% with said oligonucleotide and/or with at least one of said fragments, over the entire length of said oligonucleotide and/or fragment, respectively, and

TABLE 2

| | | | SEQ ID NO: |
|---|---|---|---|
| Iag3-2 | CACGCAGGAAATAACAGGACTT | *Salmonella* (forward) primer (claim sub-set D) | 1 |
| Iag3-2C | CAAGCATGAAATAACAGGGCTT | *Salmonella* (forward) primer (claim sub-set A) | 2 |
| Iag6-2 | GGGCAACCAGCACTAAC | *Salmonella* (reverse) primer (claim sub-set C) | 3 |
| Iag6-2C1 | GAGCAACCAGTACTAATGG | *Salmonella* (reverse) primer (claim sub-set B) | 4 |
| MBSal1spe | TGTCAGAATAGTGAGCGTGCCTTAC | *Salmonella* probe | 5 |
| MBSal1 | cgcgacTGTCAGAATAGTGAGCGTG CCTTACgtcgcg | *Salmonella* probe with one beacon arm at each end | 6 |
| CaptMod spe | AATAGTGAGCGTGCCTTACCGACG | *Salmonella* probe | 7 |
| CaptMod | cgcagcAATAGTGAGCGTGCCTTACC GACGgctgcg | *Salmonella* probe with one beacon arm at each end | 8 |

Except otherwise stated, all nucleotide sequences are given in their 5'-3' orientation.

1. Set of at Least Three, or of at Least Four Oligonucleotides, wherein said Set is Notably Useful as a Primer Set:

at least one oligonucleotide of sub-set C or of sub-set D (=sub-set C-D),
    wherein said sub-set C consists of the oligonucleotide of SEQ ID NO: 3, the conservative fragments thereof, and the conservative variants of said oligonucleotide and of said fragments, said conservative variants having a sequence identity of at least 85% with said oligonucleotide and/or with at least one of said fragments, over the entire length of said oligonucleotide and/or fragment, respectively, wherein said sub-set D consists of the oligonucleotide of SEQ ID NO: 1, the conservative fragments thereof, and the conservative variants of said oligonucleotide and of said fragments, said conservative variants having a sequence identity of at least 85% with said oligonucleotide and/or with at least one of said fragments, over the entire length of said oligonucleotide and/or fragment, respectively, wherein, for each of said three sub-sets A, B and C-D, a conservative fragment or variant of one of said three sub-sets has retained the capacity of amplifying at least one nucleic acid from the nucleic acid material of at least one *Salmonella* strain of each the seven *Salmonella* groups (groups I, II, IIIa, IIIb, IV, V, VI), preferably of each of the seven following *Salmonella* strains (=*Salmonella* reference strains):

S. *enterica* subsp. *enterica* serovar *Typhimurium* strain CIP 60.62 (group I),
S. *enterica* subsp. *salamae* strain CIP 82.29 (group II),
S. *enterica* subsp. *arizonae* strain CIP 82.30 (group IIIa),
S. *enterica* subsp. *diarizonae* strain CIP 82.31 (group IIIb),
S. *enterica* subsp. *houtanae* strain CIP 82.32 (group IV),
S. *bongori* strain CIP 82.33 (group V),
S. *enterica* subsp. *indica* strain CIP 102501 (group VI), when said conservative fragment or variant is used in multiplex with at least one oligonucleotide of each of the other two sub-sets.

Said set of oligonucleotides may comprise at least four oligonucleotides selected from:

at least one oligonucleotide of sub-set A, wherein said sub-set A consists of the oligonucleotide of SEQ ID NO: 2, the conservative fragments thereof, and the conservative variants of said oligonucleotide and of said fragments, said conservative variants having a sequence identity of at least 85% with said oligonucleotide and/or with at least one of said fragments, over the entire length of said oligonucleotide and/or fragment, respectively, at least one oligonucleotide of sub-set B, wherein said sub-set B consists of the oligonucleotide of SEQ ID NO: 4, the conservative fragments thereof, and the conservative variants of said oligonucleotide and of said fragments, said conservative variant having a sequence identity of at least 85% with said oligonucleotide and/or with at least one of said fragments, over the entire length of said oligonucleotide and/or fragment, respectively, at least one oligonucleotide of sub-set C, wherein said sub-set C consists of the oligonucleotide of SEQ ID NO: 3, the conservative fragments thereof, and the conservative variants of said oligonucleotide and of said fragments, said conservative variants having a sequence identity of at least 85% with said oligonucleotide and/or with at least one of said fragments, over the entire length of said oligonucleotide and/or fragment, respectively, at least one oligonucleotide of sub-set D, wherein said sub-set D consists of the oligonucleotide of SEQ ID NO: 1, the conservative fragments thereof, and the conservative variants of said oligonucleotide and of said fragments, said conservative variants having a sequence identity of at least 85% with said oligonucleotide and/or with at least one of said fragments, over the entire length of said oligonucleotide and/or fragment, respectively, wherein, for each one of said four sub-sets A, B, C and D, a conservative fragment or variant of one of said four sub-sets A-D has retained the capacity of amplifying at least one nucleic acid from the nucleic acid material of at least one *Salmonella* strain of each the seven *Salmonella* groups (groups I, II, IIIa, IIIb, IV, V, VI), preferably of each of the seven following *Salmonella* strains (=*Salmonella* reference strains):

S. *enterica* subsp. *enterica* serovar *Typhimurium* strain CIP 60.62 (group I),
S. *enterica* subsp. *salamae* strain CIP 82.29 (group II),
S. *enterica* subsp. *arizonae* strain CIP 82.30 (group IIIa),
S. *enterica* subsp. *diarizonae* strain CIP 82.31 (group IIIb),
S. *enterica* subsp. *houtanae* strain CIP 82.32 (group IV),
S. *bongori* strain CIP 82.33 (group V),
S. *enterica* subsp. *indica* strain CIP 102501 (group VI), when said conservative fragment or variant is used in multiplex with at least one oligonucleotide of each of the other three sub-sets.

Preferably, said conservative fragment or variant of sub-set A has retained the capacity of amplifying at least one nucleic acid from the nucleic acid material of at least one *Salmonella* strain of each the seven *Salmonella* groups (groups I, II, IIIa, IIIb, IV, V, VI), preferably of each of the seven following *Salmonella* strains (=*Salmonella* reference strains):

S. *enterica* subsp. *enterica* serovar *Typhimurium* strain CIP 60.62 (group 1),
S. *enterica* subsp. *salamae* strain CIP 82.29 (group II),
S. *enterica* subsp. *arizonae* strain CIP 82.30 (group IIIa),
S. *enterica* subsp. *diarizonae* strain CIP 82.31 (group IIIb),
S. *enterica* subsp. *houtanae* strain CIP 82.32 (group IV),
S. *bongori* strain CIP 82.33 (group V),
S. *enterica* subsp. *indica* strain CIP 102501 (group VI), when said conservative fragment or variant is used in multiplex with the oligonucleotides of SEQ ID NO: 4, 3 and 1.

Preferably, said conservative fragment or variant of sub-set B has retained the capacity of amplifying at least one nucleic acid from the nucleic acid material of at least one *Salmonella* strain of each the seven *Salmonella* groups (groups I, II, IIIa, IIIb, IV, V, VI), preferably of each of the seven following *Salmonella* strains (=*Salmonella* reference strains):

S. *enterica* subsp. *enterica* serovar *Typhimurium* strain CIP 60.62 (group I),
S. *enterica* subsp. *salamae* strain CIP 82.29 (group II),
S. *enterica* subsp. *arizonae* strain CIP 82.30 (group IIIa),
S. *enterica* subsp. *diarizonae* strain CIP 82.31 (group IIIb),
S. *enterica* subsp. *houtanae* strain CIP 82.32 (group IV),
S. *bongori* strain CIP 82.33 (group V),
S. *enterica* subsp. *indica* strain CIP 102501 (group VI), when said conservative fragment or variant is used in multiplex with the oligonucleotides of SEQ ID NO: 2, 3 and 1.

Preferably, said conservative fragment or variant of sub-set C has retained the capacity of amplifying at least one nucleic acid from the nucleic acid material of at least one *Salmonella* strain of each the seven *Salmonella* groups (groups I, II, IIIa, IIIb, IV, V, VI), preferably of each of the seven following *Salmonella* strains (=*Salmonella* reference strains):

S. *enterica* subsp. *enterica* serovar *Typhimurium* strain CIP 60.62 (group I),
S. *enterica* subsp. *salamae* strain CIP 82.29 (group II),
S. *enterica* subsp. *arizonae* strain CIP 82.30 (group IIIa),
S. *enterica* subsp. *diarizonae* strain CIP 82.31 (group IIIb),
S. *enterica* subsp. *houtanae* strain CIP 82.32 (group IV),
S. *bongori* strain CIP 82.33 (group V),
S. *enterica* subsp. *indica* strain CIP 102501 (group VI), when said conservative fragment or variant is used in multiplex with the oligonucleotides of SEQ ID NO: 2, 4 and 1.

Preferably, said conservative fragment or variant of sub-set D has retained the capacity of amplifying at least one nucleic acid from the nucleic acid material of at least one *Salmonella* strain of each the seven *Salmonella* groups (groups I, II, IIIa, IIIb, IV, V, VI), preferably of each of the seven following *Salmonella* strains (=*Salmonella* reference strains):

*S. enterica* subsp. *enterica* serovar *Typhimurium* strain CIP 60.62 (group I),
    *S. enterica* subsp. *salamae* strain CIP 82.29 (group II),
    *S. enterica* subsp. *arizonae* strain CIP 82.30 (group IIIa),
    *S. enterica* subsp. *diarizonae* strain CIP 82.31 (group IIIb),
    *S. enterica* subsp. *houtanae* strain CIP 82.32 (group IV),
    *S. bongori* strain CIP 82.33 (group V),
    *S. enterica* subsp. *indica* strain CIP 102501 (group VI), when said conservative fragment or variant is used in multiplex with the oligonucleotides of SEQ ID NO: 2, 4 and 3.

The sequence identity percentage of said conservative variant preferably is of at least 88%, more preferably of at least 91%, even more preferably of at least 93%, most preferably of at least 96%.

The skilled person can use any means that he/she finds appropriate to assess whether a given fragment or variant is conservative, i.e., whether it has retained the capacity of amplifying at least one nucleic acid from the nucleic acid material of each of said seven *Salmonella* strains, when used in multiplex with said other oligonucleotides.

For example, said fragment or variant is placed in multiplex in the same tube with said other oligonucleotides, together with the nucleic acid material of one of said seven *Salmonella* reference strains, under conditions that are favorable to said fragment or variant and said other oligonucleotides for them to act as amplification primers, to amplify at least one nucleic acid from said nucleic acid material. The same test shall be repeated with each of the six other *Salmonella* reference strains. The goal of these seven tests is to determine whether said fragment or variant can still function as an amplification primer when placed in the presence of said other oligonucleotides, and whether the resulting set still is a multiplex primer set that covers said seven reference *Salmonella* strains. If so, the candidate fragment or variant is a conservative fragment or variant.

To implement such tests, any experimental conditions that the skilled person may find appropriate can be used. Such experimental conditions notably include standard PCR experimental conditions, such as experimental conditions comprising:

placing the candidate fragment or variant with said other oligonucleotides in a tube in the presence of the nucleic acid material of one of said seven *Salmonella* reference strains, and in the presence of at least one DNA polymerase (e.g., a Taq polymerase) and of dNTP (A, C, G, T),
    performing repeated cycles of nucleic acid amplification, e.g., performing about 30-50 cycles of denaturation/annealing/elongation, for example 30-50 cycles of:
        denaturing the nucleic acid material of said *Salmonella* reference strain, for example, by heating for about 1-15 min (e.g., about 1-2 min) at a temperature of about 94-98° C. (e.g., about 94-96° C.),
        allowing said candidate fragment or variant, and said other oligonucleotides to anneal to said denatured nucleic acid material, for example, by cooling down to a temperature that is of about 5° C. below the melting points of said candidate fragment or variant and of said other oligonucleotides, typically by cooling down to a temperature of about 45-62° C. for about 20 sec. to 2 min, and optionally, activating said DNA polymerase,
        allowing the DNA polymerase to elongate any annealed primer, for example, by heating at a temperature appropriate to said DNA polymerase, e.g., at a temperature of about 72° C. for about 10-15 min.

Other experimental conditions are also described in example 1 below (real-time multiplex PCR).

Any means that the skilled person may find appropriate to detect whether amplification has occurred or not can be used. For example, said variant or fragment and said other oligonucleotides may be labeled by a detectable marker (e.g., radioactive label, fluorescent label, etc.). Preferably, one or several probes can be used to detect the presence of an amplicon. Said probe(s) can be directly or indirectly labeled, to enable an easy detection thereof. For example, a probe can bear a label (e.g., a fluorescent label) at one of its ends, either directly or indirectly (e.g., beacon probe). A preferred probe is the probe of SEQ ID NO: 6, or the sequence that is fully complementary thereto, over the entire length of said sequence of SEQ ID NO: 6. In example 1 below, experimental conditions are described which make use of the probe of SEQ ID NO: 6 in beacon format (FAM label).

Hence, as illustrated in example 1, an illustrative method to determine whether a candidate conservative variant or fragment has retained the capacity of amplifying at least one nucleic acid from the nucleic acid material of each of said seven *Salmonella* strains, when used in multiplex with said three other oligonucleotides, is a real-time multiplex PCR, which is performed for each of said seven *Salmonella* strains as follows:

preparing an amplification reaction mix having a final volume of 50 µL, comprising:
        5 µL of DNA extract of said *Salmonella* strain,
        Polymerase, preferably the Novataq Hot-Start DNA polymerase: 1 U/PCR,
        Polymerase buffer, preferably the Novataq Hot-Start DNA polymerase buffer: 1×,
        $MgCl_2$ (e.g., $MgCl_2$ Novagen): 6 mM,
        dNTP (A,C,G,T) (e.g., from Roche): 100 µM each,
        said candidate conservative variant or fragment, as well as said three other oligonucleotides (i.e., a total of four amplification primers): 300 nM each,
        the (real-time) probe of SEQ ID NO: 6, e.g., with a FAM label: 300 nM,
    submitting said amplification reaction mix to cycles of nucleic acid amplification as follows:
        cycle 1: ×1;
        cycle 2: ×50:
            15 seconds at 95° C.;
            30 seconds at 58° C.;
            30 seconds at 72° C.

If said candidate conservative variant or fragment can be considered to have retained said capacity of amplification, the four primers hybridize to a nucleic acid for each of said seven *Salmonella* strains, thereby enabling the elongation of the targeted sequence for each of said seven *Salmonella* strains. This hybridization and elongation result in the production of an amplicon, to which the real-time probe of SEQ ID NO: 6 anneals. The probe of SEQ ID NO: 6 being a beacon probe, a fluorescence signal is emitted in real-time through its FAM label. Hence, said candidate conservative variant or fragment can be considered to have retained said capacity of amplification, when a fluorescence signal can be detected for each of said seven *Salmonella* strains, and preferably when a Ct value can be measured for each of said seven *Salmonella* strains.

Preferably, said conservative fragment or variant consists of at least 14 nucleotides, more preferably of at least 15 nucleotides, even more preferably of at least 16 nucleotides.

Said conservative fragment consists of at most the total number of the parent oligonucleotide minus 1.

Preferably, said conservative variant is of at most 26 nucleotides, more preferably of at most 25 nucleotides, even more preferably of at most 24 nucleotides.

Preferably, said conservative variant consists of 14 to 26 nucleotides, more preferably of 15 to 25 nucleotides, even more preferably of 16 to 24 nucleotides.

Preferably, said conservative variant is a variant by substitution and/or deletion, more preferably by substitution or deletion, most preferably by substitution.

Preferably, said conservative variant is a variant of the reference oligonucleotide of the sub-set to which it belongs, i.e., a variant of SEQ ID NO: 2 for sub-set A, SEQ ID NO: 4 for sub-set B, SEQ ID NO: 3 for sub-set C, SEQ ID NO: 1 for sub-set D.

Preferably, said conservative variant is of the same length as the parent oligonucleotide or fragment (e.g., 22 nucleotides when SEQ ID NO: 1 or 2 is the parent oligonucleotide; 17 nucleotides when SEQ ID NO: 3 is the parent oligonucleotide; 19 nucleotides when SEQ ID NO: 4 is the parent oligonucleotide).

Based on a sequence identity of at least 85%, the number of oligonucleotide variation(s) can be e.g., of:
1 to 4, with respect to SEQ ID NO: 1;
1 to 4, with respect to SEQ ID NO: 2;
1 to 3, with respect to SEQ ID NO: 3;
1 to 3, with respect to SEQ ID NO: 4.

Said set may consist of three or four oligonucleotides.
Preferably, said set comprises:
the oligonucleotide of SEQ ID NO: 2,
the oligonucleotide of SEQ ID NO: 4,
the oligonucleotide of SEQ ID NO: 3, and
the oligonucleotide of SEQ ID NO: 1.

2. Set of at Least Two Oligonucleotides, wherein Said Set is Notably Useful as a Primer Set (or as a Primer Pair, if only Two Oligonucleotides are Present in Said Set):

The invention also relates to sets of oligonucleotides, which comprises at least two oligonucleotides selected from the above-mentioned set of at least three, or of at least four oligonucleotides.

In a set of at least two oligonucleotides:
one of said at least two oligonucleotides is an oligonucleotide of said above-mentioned sub-set A, and
the other of said at least two oligonucleotides is an oligonucleotide of said above-mentioned sub-set B, C or D, preferably an oligonucleotide of said sub-set B or C, more preferably an oligonucleotide of said sub-set B.

In another set of at least two oligonucleotides:
one of said at least two oligonucleotides is an oligonucleotide of said above-mentioned sub-set B, and
the other of said at least two oligonucleotides is an oligonucleotide of said above-mentioned sub-set A, C or D, preferably an oligonucleotide of said sub-set A or D, more preferably an oligonucleotide of said sub-set A.

Said sets may consist of two oligonucleotides, more particularly of a pair of forward and reverse primers (see table 2 above).

In each of the sets of at least two oligonucleotides:
a preferred oligonucleotide of sub-set D is the oligonucleotide of SEQ ID NO: 1,
a preferred oligonucleotide of sub-set B is the oligonucleotide of SEQ ID NO: 4,
a preferred oligonucleotide of sub-set C is the oligonucleotide of SEQ ID NO: 3,
a preferred oligonucleotide of sub-set A is the oligonucleotide of SEQ ID NO: 2.

A preferred set of at least two oligonucleotides comprises:
the oligonucleotide of SEQ ID NO: 2 and
the oligonucleotide of SEQ ID NO: 4 or of SEQ ID NO: 3, preferably of SEQ ID NO: 4.

Another preferred set of at least two oligonucleotides comprises:
the oligonucleotide of SEQ ID NO: 4 and
the oligonucleotide of SEQ ID NO: 1, or of SEQ ID NO: 2, preferably of SEQ ID NO: 2.

3. Individual Oligonucleotides, which are Notably Useful as Primers:

The application also relates to each of the oligonucleotides that are herein described, individually as a product, more particularly as a product that is notably useful as primer and/or probe.

The invention more particularly relates to an oligonucleotide, which is selected from the above-mentioned set of at least four oligonucleotides (see §1 above).

The application thus relates to an oligonucleotide of sub-set A, preferably to the oligonucleotide of SEQ ID NO: 2. Such an oligonucleotide is notably useful as a primer or a probe, preferably as a primer.

The application also relates to an oligonucleotide of sub-set B, preferably to the oligonucleotide of SEQ ID NO: 4. Such an oligonucleotide is notably useful as a primer or a probe, preferably as a primer.

4. Oligonucleotides, which are Notably Useful as Probes, more Particularly as Real-Time Probes:

The application also relates to an oligonucleotide, which is:
i. the oligonucleotide of SEQ ID NO: 5,
ii. the complementary oligonucleotide thereof, the sequence of which is fully complementary to the oligonucleotide of SEQ ID NO: 5, over the entire length of said oligonucleotide of SEQ ID NO: 5,
iii. a conservative fragment of the oligonucleotide of i. or ii.,
iv. a conservative variant of the oligonucleotide of i. or ii., or of a fragment of iii.,
wherein said conservative fragment or variant has retained the capacity of hybridizing to the genomic DNA or to the cDNA of at least one *Salmonella* strain of each the seven *Salmonella* groups (groups I, III, IIIa, IIIb, IV, V, VI), preferably to the genomic DNA or to the cDNA of each of the seven following *Salmonella* strains (=*Salmonella* reference strains):
*S. enterica* subsp. *enterica* serovar *Typhimurium* strain CIP 60.62 (group I),
*S. enterica* subsp. *salamae* strain CIP 82.29 (group II),
*S. enterica* subsp. *arizonae* strain CIP 82.30 (group IIIa),
*S. enterica* subsp. *diarizonae* strain CIP 82.31 (group IIIb),
*S. enterica* subsp. *houtanae* strain CIP 82.32 (group IV),
*S. bongori* strain CIP 82.33 (group V),
*S. enterica* subsp. *indica* strain CIP 102501 (group VI),
when said conservative fragment or variant is used under hybridization conditions that are at least highly stringent conditions.

Preferably, said oligonucleotide is the oligonucleotide of SEQ ID NO: 5, or the complementary oligonucleotide thereof.

Such an oligonucleotide is notably useful as a probe.

Such an oligonucleotide is especially adapted to be used in real-time amplification with the above-mentioned set of at least three, or of at least four, oligonucleotides, to detect *Salmonella* strains of groups I, II, IIIa, IIIb, IV, V and VI.

Highly stringent conditions or very highly stringent conditions are as intended by the person of average skill in the art.

Illustrative conditions of highly stringent conditions comprise:

hybridization to filter-bound DNA in 5×SSC, 2% sodium dodecyl sulfate (SDS), 100 micrograms/mL single stranded DNA at 55-65° C. for 8 hours, and washing in 0.2×SSC and 0.2% SDS at 60-65° C. for thirty minutes.

Illustrative conditions of very highly stringent conditions comprise:

hybridization to filter-bound DNA in 5×SSC, 2% sodium dodecyl sulfate (SDS), 100 micrograms/mL single stranded DNA at 55-65° C. for 8 hours, and washing in 0.1×SSC and 0.1% SDS at 60-65° C. for thirty minutes.

Illustrative of such conditions are also the PCR conditions described in example 1 below.

Preferably, said conservative variant has a sequence identity of at least 85% with said oligonucleotide of i. or ii., or with a fragment of iii., over the entire length of said oligonucleotide or fragment.

Said conservative fragment consists of at most the total number of the parent oligonucleotide minus 1.

Preferably, said conservative fragment or variant is of at least 20 nucleotides, preferably of at least 21 nucleotides, more preferably of at least 22 nucleotides.

Preferably, said conservative variant is of at most 29 nucleotides, preferably of at most 28 nucleotides, more preferably of at most 27 nucleotides.

Preferably, said conservative variant consists of 20 to 29 nucleotides, more preferably of 21 to 28 nucleotides, even more preferably of 22 to 27 nucleotides.

Preferably, said conservative variant is a variant by substitution and/or deletion, preferably by substitution or deletion, more preferably by substitution.

Preferably, said conservative variant has the same length as the parent oligonucleotide or fragment.

Based on a sequence identity of at least 85%, the number of oligonucleotide variation(s) can be e.g., of 1 to 4, with respect to SEQ ID NO: 5.

When used as a probe, such an oligonucleotide has the special advantage of enabling to detect *Salmonella* strains of groups I, II, IIIa, IIIb, IV, V and VI. It further enables to detect all group I serovars, and notably the following *S. enterica* subsp. *enterica* serovars: *S. Typhimurium*, *S. Typhi*, *S. Paratyphi*, *S. Virchow*, *S. Hadar*, *S. Enteritidis*, *S. Anatum*, *S. Senftenberg*, *S. Cerro*, *S. Poona*, *S. Grumpensis*, *S. Dalhem*, *S. Kentucky*, *S. Lomita*, *S. Kirkee*, *S. Bredeney*, *S. Carrau*, *S. Aberdeen*, *S. Tenessee*.

When said oligonucleotide is used as a probe, it may be linked to at least one detection label, and/or at least one nucleotide arm that is unrelated to *Salmonella* and that is intended to carry a quencher or a reporter (e.g., a fluorophore), such as at least one beacon arm. In such a structure, said oligonucleotide is the hybridizing or "specific" portion, whilst the remaining elements have a function in the detection of the hybridized nucleic acid.

For example, when the oligonucleotide of SEQ ID NO: 5 is linked to beacon arms at its 5' and 3' ends, it may have the sequence of SEQ ID NO: 6, or the complementary oligonucleotide thereof, the sequence of which is fully complementary to the oligonucleotide of SEQ ID NO: 6, over the entire length of said oligonucleotide of SEQ ID NO: 6. Said beacon arm-linked of SEQ ID NO:6 or the complementary sequence thereof, may advantageously bear a reporter (e.g., a fluorophore) at one of its end, and a quencher at the other end.

Various formats (types) of probes, including Taqman™ probes (hydrolysis probes), Molecular Beacons™ (beacon probes or molecular beacon probes), and Scorpion™ probes are known in the art.

It may e.g., be linked to at least one beacon arm, or to at least one Scorpion™ arm, preferably at least one of such arms in 5' and/or 3', most preferably two of such arms, in 5' and in 3', respectively.

One of preferred formats is the beacon format.

The structure of molecular beacons is as follows. A short nucleotide sequence (so-called beacon arm) which is unrelated to the target sequence is thus covalently linked to both ends of the probe.

The overall sequence of this arm is not related to *Salmonella*, which does not exclude the situation where one or two of the nucleotide(s) that are comprised within this arm may hybridize to complementary nucleotide(s) located on the *Salmonella* nucleic acid strand.

A short unrelated arm is thus linked in 5' of the probe, and is labelled with a fluorescent moiety (i.e. fluorescent dye or fluorescent marker). Another but still unrelated arm is linked to the 3' end of probe and is labelled with a fluorescence quenching moiety. Thus, molecular beacons have a fluorophore and a quencher at opposite ends. The 5' short arm is totally complementary to the one in 3' so that they can anneal together, and thus can assume a hairpin structure when unhybridized to the target in solution. In this hairpin conformation, the quencher and the fluorescent dye are close enough to each other to allow efficient quenching of the fluorophore. However, when the probe encounters a target molecule, annealing is favoured with respect to the hairpin conformation when values of beacon arm Tm and probe Tm are suitably chosen (theoretically: probe Tm>beacon arm Tm>primer Tm, wherein Tm is the melting temperature of interest). The fluorophore and quencher move away from each other and the fluorophore can then fluoresce when illuminated by suitable light excitation. As PCR proceeds, amplification product accumulates, and the amount of fluorescence at any given cycle depends on the amount of amplification product present at that time. (See e.g., Sanjay Tyagi and Fred Russell Kramer, Nature Biotechnology 1996, volume 14, pages 303-308; Nature Biotechnology 1998, volume 16, pages 49-53).

(Remark: It is also possible to link the fluorophore at the 3' end, while attaching the quencher at the 5' end).

Schematically, said probe can have the following formulae (molecular beacon format):

5' Fluorophore-(arm1)-probe-(arm2)-Quencher 3'
5' Quencher-(arm1)-probe-(arm2)-Fluorophore 3' wherein arm1 and arm2 can be any short nucleotide sequences, e.g. in the range of 3-10 nucleotides, preferably 5, 6, 7 nucleotides, allowing for the hairpin structure formation under suitable stringency conditions, i.e. arm1 and arm2 are totally complementary to anneal under the desired stringency conditions (standard PCR stringency conditions include, for example, an annealing temperature of 55 to 65° C. and an Mg concentration of 2 to 7 mM). However, arm1 and arm2 are unrelated to the target sequence of the probe, i.e., the hairpin conformation resulting from the annealing between arm1 and arm2 is essentially the only possible secondary structure for the probe when unhybridized. The skilled person would know how to choose such arms for a given probe.

By fluorophore, it is herein understood any fluorescent marker/dye known in the art. Examples of such suitable fluorescent markers include Fam, Hex, Tet, Joe, Rox, Tamra, Max, Edans, Cy dyes such as Cy5, Fluorescein, Coumarin, Eosine, Rhodamine, Bodipy, Alexa, Cascade Blue, Yakima Yellow, Lucifer Yellow and Texas Red (all of them are Trade-Marks), the family of ATTO dyes.

By quencher, we herein understand any quencher known in the art. Examples of such quenchers include Dabcyl, Dark Quencher, Eclipse Dark Quencher, ElleQuencher, Tamra, BHQ and QSY (all of them are Trade-Marks).

The skilled person would know which combinations of dye/quencher are suitable when designing a probe.

5. Set of Oligonucleotides, which Comprises at Least One of Said Oligonucleotides, which are Notably Useful as Probes:

The application relates to a set of oligonucleotides, which comprises at least one of the above-mentioned oligonucleotides, which are notably useful as probes (see §4 above), i.e., a set of oligonucleotides, which comprises at least one oligonucleotide, which is:

i. the oligonucleotide of SEQ ID NO: 5,
  ii. the complementary oligonucleotide thereof, the sequence of which is fully complementary to the oligonucleotide of SEQ ID NO: 5, over the entire length of said oligonucleotide of SEQ ID NO: 5,
  iii. a conservative fragment of the oligonucleotide of i. or ii.,
  iv. a conservative variant of the oligonucleotide of i. or ii., or of a fragment of iii., wherein said conservative fragment or variant has retained the capacity of hybridizing to the genomic DNA or to the cDNA of at least one *Salmonella* strain of each the seven *Salmonella* groups (groups I, II, IIIa, IIIb, IV, V, VI), preferably to the genomic DNA or to the cDNA of each of the seven following *Salmonella* strains (=*Salmonella* reference strains):

*S. enterica* subsp. *enterica* serovar *Typhimurium* strain CIP 60.62 (group I),
  *S. enterica* subsp. *salamae* strain CIP 82.29 (group II),
  *S. enterica* subsp. *arizonae* strain CIP 82.30 (group IIIa),
  *S. enterica* subsp. *diarizonae* strain CIP 82.31 (group IIIb),
  *S. enterica* subsp. *houtanae* strain CIP 82.32 (group IV),
  *S. bongori* strain CIP 82.33 (group V),
  *S. enterica* subsp. *indica* strain CIP 102501 (group VI), when said conservative fragment or variant is used under hybridization conditions that are at least highly stringent conditions.

Preferably, said at least one oligonucleotide is:
the oligonucleotide of SEQ ID NO: 5, or the complementary oligonucleotide thereof, optionally linked to at least one detection label and/or at least one nucleotide arm that is unrelated to *Salmonella* and that is intended to carry a quencher or a reporter, or is
the oligonucleotide of SEQ ID NO: 6, or the complementary oligonucleotide thereof, optionally linked to a reporter and a quencher.

In addition to said at least one oligonucleotide, said set may further comprise at least one other oligonucleotide, which is intended as a probe, such as the probe of SEQ ID NO: 7 or of SEQ ID NO: 8.

Said at least one oligonucleotide, the sequence of which is of SEQ ID NO: 5 or of SEQ ID NO: 6 or the complementary sequences thereof, can be considered as enabling to detect any bacterium, which is of the genus *Salmonella*. In addition to such an oligonucleotide, at least one other oligonucleotide, which is specific of one or several strain(s) and/or serovar(s) and/or subspecies and/or species, can be used, preferably in multiplex with said at least one genus-specific oligonucleotide.

The resulting set of oligonucleotides advantageously enables to determine whether the tested sample contains a *Salmonella* bacterium, and also to determine which strain(s), serovar(s), subspecies and/or species is present in said sample. Such a determination is especially useful for diagnostic applications. For example, at least one other oligonucleotide, which is specific of the serovar(s) *Typhi* and/or *Paratyphi*, can be used; such an oligonucleotide set is especially useful to determine whether a bacterium of the genus *Salmonella* is present in the tested sample, and whether these *Salmonella* bacteria does or not comprise bacteria that are causative of typhoid fever or paratyphoid fever.

In addition to said at least one oligonucleotide, said set may further comprise at least one other oligonucleotide, which is intended as a primer, such as at least one oligonucleotide selected from one of the above-mentioned sets of at least four oligonucleotides (see §1 above). In addition to said at least one oligonucleotide, said set may further thus comprise at least one other oligonucleotide, which is selected from the oligonucleotides of SEQ ID NO: 1, SEQ ID NO: 2, SEQ ID NO: 3, SEQ ID NO: 4.

Advantageously, in addition to said at least one oligonucleotide, said set further comprises at least one of the above-mentioned individual oligonucleotides (see §3 above).

Advantageously, in addition to said at least one oligonucleotide, said set further comprises at least one of the above-mentioned sets of at least two oligonucleotides (see §2 above).

Very advantageously, in addition to said at least one oligonucleotide, said set further comprises at least one of the above-mentioned sets of at least four oligonucleotides (see §1 above).

Preferably, said set comprises:
the oligonucleotide of SEQ ID NO: 5, or the complementary oligonucleotide thereof, optionally linked to at least one detection label and/or at least one nucleotide arm that is unrelated to *Salmonella* and that is intended to carry a quencher or a reporter (such as e.g., the oligonucleotide of SEQ ID NO: 6, or the complementary oligonucleotide thereof, optionally linked to a quencher and a reporter), and
the oligonucleotide of SEQ ID NO: 2, and
the oligonucleotide of SEQ ID NO: 4.

More preferably, said set comprises:
the oligonucleotide of SEQ ID NO: 5, or the complementary oligonucleotide thereof, optionally linked to at least one detection label and/or at least one nucleotide arm that is unrelated to *Salmonella* and that is intended to carry a quencher or a reporter, (such as e.g., the oligonucleotide of SEQ ID NO: 6, or the complementary oligonucleotide thereof, optionally linked to a quencher and a reporter), and
the oligonucleotide of SEQ ID NO: 2, and
the oligonucleotide of SEQ ID NO: 4, and
the oligonucleotide of SEQ ID NO: 3, and
the oligonucleotide of SEQ ID NO: 1.

Said set is notably useful as a set of primers and probe(s), wherein, e.g., the oligonucleotide of SEQ ID NO: 5 or the complementary oligonucleotide thereof can be used as a probe, whereas the oligonucleotides of SEQ ID NO: 2, 4, 3 and 1 can be used as primers (more particularly as multiplex primers).

Advantageously, said set is useful as a real-time amplification oligonucleotide set (see the examples below).

6. Amplification Mix and Kits:

The application also relates to an amplification mix, and to a kit, wherein said amplification mix or kit comprises:
at least one above-mentioned set of at least four oligonucleotides (see §1 above), and/or at least one above-mentioned set of at least two oligonucleotides (see §2 above), and/or at least one above-mentioned individual oligonucleotide (see §3 above), and/or at least one above-mentioned oligonucleotide, which is notably useful as a probe (see §4 above) (including at least one genus-specific oligonucleotide and at least one oligonucleotide, which is specific of one or more strain(s) and/or serovar(s) and/or subspecies and/or species), at least one above-mentioned set of oligonucleotides as above-described in §5.

Said amplification mix or kit may further comprise at least one element among the following elements:

at least nucleic acid (e.g., DNA) extraction solution (e.g., a nucleic acid extraction buffer or sub-kit), at least one DNA polymerase (e.g., a Taq polymerase), at least one dNTP, preferably at least one of the four dNTP (A, C, G, T), at least one buffer having a pH adapted to the polymerase activity of said at least one DNA polymerase, at least one instruction leaflet advising of performing a real-time multiplex amplification, to detect *Salmonella*, buffered peptone water.

In the kit according to the invention, the oligonucleotides (primers, probes) can be either kept separately, or partially mixed, or totally mixed.

Said oligonucleotides can be provided under dry form, or solubilized in a suitable solvent, as judged by the skilled person. Suitable solvents include TE, PCR-grade water, and the like.

In a preferred embodiment, the kit according to the invention can also contain further reagents suitable for a PCR step.

Such reagents are known to those skilled in the art, and include water, like nuclease-free water, RNase free water, DNAse-free water, PCR-grade water; salts, like magnesium, potassium; buffers such as Tris; enzymes, including polymerases, such as Taq, Vent, Pfu (all of them Trade-Marks), activable polymerase, and the like; nucleotides like deoxynucleotides, dideoxunucleotides, dNTPs, dATP, dTTP, dCTP, dGTP, dUTP; other reagents, like DTT and/or RNase inhibitors; and polynucleotides like polyT, polydT, and other oligonucleotides, e.g., primers.

In another preferred embodiment, the kit according to the invention comprises PCR controls. Such controls are known in the art, and include qualitative controls, positive controls, negative controls, internal controls, quantitative controls, internal quantitative controls, as well as calibration ranges. The internal control for said PCR step can be a template which is unrelated to the target template in the PCR step. Such controls also may comprise control primers and/or control probes. For example, in the case of HPV detection, it is possible to use as an internal control, a polynucleotide chosen within a gene whose presence is excluded in a sample originating from a human body (for example, from a plant gene), and whose size and GC content is equivalent to those from the target sequence.

Such a kit is notably useful for the detection of *Salmonella*.

More particularly, such a kit is useful for the detection of *Salmonella* in a product intended for human and/or animal consumption, and/or in a biological sample originating from a human or animal.

Advantageously, said kit is useful to check the safety of a food and/or beverage product, or of a product that is used in the manufacture of a food and/or beverage product.

Advantageously, said kit is a kit for the diagnosis of salmonellosis, more particularly of typhoid and/or paratyphoid fever.

7. Amplicons:

The application also relates to any amplicon, which is obtainable from a *Salmonella* strain belonging to group I, II, IIIa, IIIb, IV, V or VI, by amplification with a set of at least four oligonucleotides of any one of claims 1-3.

Said strain may e.g., be one of the above-mentioned seven reference strains. It preferably is a strain that naturally-occurs on a product intended for human and/or animal consumption, or a strain that naturally-occurs in a human or animal infected by *Salmonella*, such as e.g., a salmonellosis patient (including typhoid fever).

The application also relates to any amplification composition, which comprises at least one of such amplicons.

8. Processes:

The application also relates to a process for the detection of *Salmonella* in a sample.

The process of the invention comprises:
optionally, homogenizing said sample (especially, when said sample is solid, see the "background of the invention" section), optionally, incubating said sample, or said homogenized sample, in buffered peptone water for 18±2 hours, e.g., at 37±1° C., (see the pre-enrichment step, as above-described in the "background of the invention" section), said incubation in buffered peptone water being especially recommended for samples of products intended for human and/or animal consumption, more particularly for food, beverage samples and/or environmental samples.

optionally, extracting the nucleic acids from said sample, or from said homogenized sample, or from the pellet recovered by centrifugation of said peptone-incubated sample, submitting said sample or homogenized sample or pellet, or a nucleic acid extract thereof, to nucleic acid amplification using the four oligonucleotides contained in one of said above-mentioned set of at least four oligonucleotides (see §1 above), as primers, detecting whether an amplicon has been, or is, produced by said nucleic acid amplification, whereby a positive detection is indicative of the fact that at least one *Salmonella* is present in said sample.

Preferably, said four oligonucleotides are:
the oligonucleotide of SEQ ID NO: 2,
the oligonucleotide of SEQ ID NO: 4,
the oligonucleotide of SEQ ID NO: 3, and
the oligonucleotide of SEQ ID NO: 1.

Unless the *Salmonella* content of the sample is highly diluted, a negative detection will be indicative of the fact that no *Salmonella* is present in said sample.

Said sample can be a sample of any material that is susceptible of, or suspected of, containing at last one *Salmonella* bacterium.

Such material notably comprises food, beverage, intended for animal or human consumption.

Illustrative food or beverage notably comprises milk, and milk-derived product, such as yoghourt, fermented milk, cheese.

Illustrative food or beverage also comprises other food or beverage of animal origin, such as delicatessen, meat, poultry, eggs, as well as green vegetables (which may have been contaminated from manure).

The material to be analyzed can be a biological sample collected from a patient or an animal, suspected of being infected by *Salmonella*. Such biological samples notably include gastro-enteric samples, such as feces, or blood, serum, plasma.

A swab soaked with human stool can be inoculated to selenite-cystine broth, overnight at 37° C. Then incubated broth can be used for *Salmonella* detection in multiplex PCR.

If this material is solid (e.g., in foods), it can be grinded, pounded or otherwise broken, and/or homogenized, to facilitate access to the nucleic acids that may be contained herein. ISO standards are available, which describe methods of preparing a product to a bacterial analysis. For milk products, the ISO standard is ISO 8261.

The goal is to make nucleic acids that may be contained in the material accessible to primers for them to anneal thereof, thereby allowing elongation of the annealed nucleic acid.

Before implementation of the amplification method, the material to be analyzed can be pre-treated to enrich the material in *Salmonella* cells to facilitate their detection. Accordingly, such a pre-enrichment step is usually performed when the *Salmonella* contamination is very low.

Such a pre-treatment step can e.g., be the standard pre-enrichment step that is described in Standard ISO 6579:2002, i.e., by placing 25 grams of said material in 225 mL of buffered peptone water (pH 7.0±0.2 at 25° C. after sterilization), and incubating it at 37±1° C. for 18±2 hours.

When the material contains a relatively high amount of cocoa (e.g., at least 20%), it is recommended to add 50 g/L of casein or 100 g/L of powder skimmed milk in aid buffered peptone water, and especially when the material is likely to be contaminated by Gram-positive microorganisms, to add 0.018 g/l of brilliant green after 2 hours of incubation. Especially for PCR applications, a re-growing step in buffer peptone water can be added to avoid PCR inhibition.

It is also recommended to take care that the pH does not decrease below 4.5 during said pre-enrichment.

At the end of the pre-enrichment step, the medium is centrifuged, to recover the pellet.

Preferably, the pellet is submitted to nucleic acid extraction, e.g., to DNA extraction, to recover the nucleic acid extract of the pre-enriched medium. Any nucleic acid extraction means that the skilled person may find appropriate can be used, such as the "InstaGen Matrix" product that is available from Bio-Rad (Bio-Rad, Hercules, U.S.A.; product reference 732-6030).

The method of the invention may comprise such a pre-enrichment step, in accordance with said ISO standard, whereby the amplification step is then performed on a sample of the pre-enriched medium that is obtained from said pre-enrichment step, or a nucleic acid extract thereof.

The oligonucleotides of the invention have nevertheless the special advantage of enabling to avoid this pre-enrichment step. Indeed, the invention provides oligonucleotides that are so sensitive in amplifying and detecting *Salmonella* that such a pre-enrichment step may, in many circumstances, be unnecessary. Under such circumstances, the amplification step is directly performed on a sample of said material (or on a dilution thereof or on a liquid homogenizate thereof), without any pre-enrichment step, preferably on a nucleic acid extract thereof.

Hence, in accordance with an advantageous embodiment of the invention, said sample or said homogenized sample does not need to be incubated in buffered peptone water for 18±2 hours.

Preferably, said amplicon detection is performed by using at least one of the oligonucleotides described in §4, as a probe. Such a probe will anneal to said amplicon, if said amplicon is present in the test tube.

Advantageously, said probe is
the oligonucleotide of SEQ ID NO: 5, or the complementary oligonucleotide thereof, optionally linked to at least one detection label and/or at least one nucleotide arm that is unrelated to *Salmonella* and that is intended to carry a quencher or a reporter, or
the oligonucleotide of SEQ ID NO: 6, or the complementary oligonucleotide thereof, optionally linked to a reporter and a quencher.

Advantageously, such a probe is such a wide *Salmonella* coverage, that said amplicon detection does not require to use any other probe (see examples below: the beacon probe of SQ ID NO: 6—whose hybridizing portion is the oligonucleotide of SEQ ID NO: 5—detects the seven *Salmonella* reference strains; the probe of SEQ ID NO: 7 or 8 can be used with it, but would be redundant).

Preferably, the process of the invention is a real-time amplification process. Indeed, every single oligonucleotide that is described in the present application has been designed and built to enable an implementation in a multiplex of primers, preferably in a multiplex of primers and probe for real-time amplification.

Said *Salmonella* detection process can be easily used in routine in a clinical environment, such as a hospital, and will be very useful for the diagnosis of salmonellosis.

The application also relates to a process for checking the safety of products that are intended for human and/or animal consumption, more particularly the safety of a food and/or beverage product, or of a product that is used in the manufacture of a food and/or beverage product.

Such a process comprises submitting said product to be analyzed, or a sample thereof, to the *Salmonella* detection process of the invention. A positive detection will be indicative of the fact that it is not recommended to use said product for human and/or animal consumption.

The term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited. The term "essentially consisting of" is a partially open term, which does not exclude additional, unrecited element(s), step(s), or ingredient(s), as long as these additional element(s), step(s) or ingredient(s) do not materially affect the basic and novel properties of the invention.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the present application, meant as more particularly encompassing the term "consisting of" ("consist(s) of"), and the term "essentially consisting of" ("essentially consist(s) of").

Each of the relevant disclosures of all references cited herein is specifically incorporated by reference. The following examples are offered by way of illustration, and not by way of limitation.

EXAMPLES

Example 1

Comparative Example

Panel of *Salmonella* Strains

This example compares the *Salmonella* detection range (=inclusivity), and the sensitivity of different real-time PCR oligonucleotide sets.

A panel of reference *Salmonella* strains covering groups II, IIIa, IIIb, IV, VI, were assayed by real-time PCR, using four different sets of oligonucleotides:
- SET 1: primers SEQ ID NO: 1 and 3 (primers lag3-2 and lag6-2)+probe SEQ ID NO: 8 (probe CaptMod);
- SET 2: primers SEQ ID NO: 1, 2, 3, 4 (primers lag3-2, lag6-2, lag3-2C, lag6-2C1) and probe SEQ ID NO: 8 (probe CaptMod);
- SET 3: primers SEQ ID NO: 1, 2, 3, 4 (primers lag3-2, lag6-2, lag3-2C, lag6-2C1) and probe SEQ ID NO: 6 (probe MBSal1);
- SET 4: primers SEQ ID NO: 1, 2, 3, 4 (primers lag3-2, lag6-2, lag3-2C, lag6-2C1) and probes SEQ ID NO: 6 and 8 (probes CaptMod and MB Sal1).

Real-time PCR oligonucleotide sets 2, 3 and 4 are oligonucleotide sets of the invention, whereas real-time PCR oligonucleotide set 1 is not a set of the invention.

Reference *Salmonella* strains covering groups II to VI are:

TABLE 3

| Strain (group) | CIP n° |
| --- | --- |
| *S. enterica* subsp. *salamae* (II) | CIP 82.29 |
| *S. enterica* subsp. *arizonae* (IIIa) | CIP 82.30 |
| *S. enterica* subsp. *diarizonae* (IIIb) | CIP 82.31 |
| *S. enterica* subsp. *houtanae* (IV) | CIP 82.32 |
| *S. bongori* (V) | CIP 82.33 |
| *S. enterica* subsp. *indica* (VI) | CIP 102501 |

Each of these strains is available from the C.N.C.M. (Collection Nationale de Cultures de Microorganismes; Institut Pasteur; 25, rue du Docteur Roux; F-75724 Paris Cedex 15; France). The CIP number is the C.N.C.M. strain deposit number.

Cell Cultures:

Each reference strain has been grown on 10 mL of Tryptone Soy Broth (TSB, Bio-Rad, ref. 355-3454) for 16 h at 37° C. (at least $1.10^6$ cfu/mL at the end of the culture). Each tube was inoculated with a colony picked with a 10 µL culture loop.

DNA Extraction:

1 mL of each culture was centrifuged at 10,000 g for 5 minutes in 1.5 mL Eppendorf tubes. The supernatants were discarded. 200 µL of the InstaGen matrix (available from Bio-Rad, Hercules, U.S.A.; product reference 732-6030) were added to the bacterial pellet. A vortex step was done to homogenise the solution. The tubes were then incubated for 10 minutes at 95° C.

5 µL of the extracted DNA is used in PCR.

PCR:

Composition of the amplification reaction mix:
Final reaction volume: 50 µL (45 µL of reaction mix+5 µL of DNA extract)
Novataq Hot-Start DNA polymerase: 1 U/PCR
Novataq Hot-Start DNA polymerase buffer: 1×
$MgCl_2$ Novagen: 6 mM
dNTP (A,C,G,T) (from Roche): 100 µM each
Primers: 300 nM each
Probe(s) (FAM label): 300 nM each
Thermal Cycle:
Amplification and detection were achieved by real-time PCR using an iCycler iQ (Bio-Rad).
Cycle 1: ×1
  10 min at 95° C. (denaturation of bacterial genomic DNA and activation of Taq polymerase)
Cycle 2: ×50
  15 seconds at 95° C.—denaturation of bacterial genomic DNA
  30 seconds at 58° C.—detection of the fluorescence
  30 seconds at 72° C.—elongation

*Salmonella* Detection Range:

The detection of each of the *Salmonella* strains was monitored by real-time PCR.

Sensitivity:

*Salmonella* reference strains were recovered after cell culture as described above. Each of the *Salmonella* reference strains was then diluted at $10^{-5}$, $10^{-6}$, $10^{-7}$ and $10^{-8}$ in buffered peptone water (Buffered Peptone Water, Bio-Rad, ref. 355-4179).

DNA was thereafter extracted using the above-mentioned DNA extraction kit, and submitted to real-time PCR with each of said oligonucleotide sets, as described above.

*Salmonella* Detection Range Results:

The real-time PCR curves obtained with each of the six reference strains are shown in FIGS. 1-6.

The results were also qualified:
- "−", when the *Salmonella* strain was not detected;
- "+", when *Salmonella* was detected, but with a low level of fluorescence signal and a given Cycle Threshold (Ct) value (SET 1 and SET 2 results).
- "++", when *Salmonella* was detected with a correct level of fluorescence signal and a better Cycle Threshold (Ct) value (SET 3 and SET 4 results compared to the SET 1 and SET 2 results).

Representative results are shown in table 4 below:

TABLE 4

| | | Primers: | | | |
| --- | --- | --- | --- | --- | --- |
| | | lag3-2/lag6-2 SEQ ID NO: 1 and 3 | lag3-2/lag6-2/lag3-2C/lag6-2C1 SEQ ID NO: 1, 2, 3 and 4 | | |
| | | Probe(s): | | | |
| | | CaptMod SEQ ID NO: 8 | CaptMod SEQ ID NO: 8 | MBSal1 SEQ ID NO: 6 | CaptMod + MBSal1 SEQ ID NO: 8 and 6 |
| | | SET n°: | | | |
| Strain (group) | | SET 1 (not of the invention) | SET 2 (of the invention) | SET 3 (of the invention) | SET 4 (of the invention) |
| *S. enterica* subsp. *salamae* (II) | CIP 82.29 | + | + | ++ | ++ |
| *S. enterica* subsp. *arizonae* (IIIa) | CIP 82.30 | − | − | ++ | ++ |
| *S. enterica* subsp. *diarizonae* (IIIb) | CIP 82.31 | + | + | ++ | ++ |
| *S. enterica* subsp. *houtanae* (IV) | CIP 82.32 | − | − | ++ | ++ |

TABLE 4-continued

| Strain (group) | | Primers: | | | |
|---|---|---|---|---|---|
| | | lag3-2/lag6-2 SEQ ID NO: 1 and 3 | lag3-2/lag6-2/lag3-2C/lag6-2C1 SEQ ID NO: 1, 2, 3 and 4 | | |
| | | Probe(s): | | | |
| | | CaptMod SEQ ID NO: 8 | CaptMod SEQ ID NO: 8 | MBSal1 SEQ ID NO: 6 | CaptMod + MBSal1 SEQ ID NO: 8 and 6 |
| | | SET n°: | | | |
| | | SET 1 (not of the invention) | SET 2 (of the invention) | SET 3 (of the invention) | SET 4 (of the invention) |
| S. bongori (V) | CIP 82.33 | − | + | ++ | ++ |
| S. enterica subsp. indica (VI) | CIP 102501 | + | + | ++ | ++ |

Both FIGS. 1-6 and table 4 demonstrate that:

Oligonucleotide set 1 enables to detect only 3 of the 6 Salmonella strains.

Oligonucleotide set 2 enables to detect 4 of the 6 Salmonella strains: when compared to set 1, the results of oligonucleotide set 2 show that using the primers of SEQ ID NO: 2 and 4, in addition to primers SEQ ID NO: 1 and 3, improves the Salmonella detection range, compared to using primers SEQ ID NO: 1 and 3 only.

Oligonucleotide set 3 enables to detect all the strains (6/6): when compared to set 2, the results of set 3 show that using the probe of SEQ ID NO: 6 drastically improves the detection range, compared to using the probe of SEQ ID NO: 8.

The performances of oligonucleotide set 4 are equivalent to the ones of oligonucleotide set 3; using the probe of SEQ ID NO: 8, in addition to the probe of SEQ ID NO: 6, does not improve the detection range, but does not alter it.

Sets 2, 3 and 4 have a better detection range than set 1.

The best results are obtained using set 3 or set 4.

Sensitivity Results:

The sensitivity of set 1 was compared to the one of set 3, by assaying each of these two sets on a dilution range of each of said six reference Salmonella strains.

Representative results are reported in Table 5:

TABLE 5

| | Strain | | | | | | | | | | | |
|---|---|---|---|---|---|---|---|---|---|---|---|---|
| | S. salamae CIP 82.29 (group II) | | | | S. arizonae CIP 82.30 (group IIIa) | | | | S. diarizonae CIP 82.31 (group IIIb) | | | |
| Dilution | Ct with Set 1 | Ct with Set 3 | cfu/ mL | cfu/ PCR | Ct with Set 1 | Ct with Set 3 | cfu/ mL | cfu/ PCR | Ct with Set 1 | Ct with Set 3 | cfu/ mL | cfu/ PCR |
| $10^{-5}$ | 31.3 | 29.42 | 9700 | 250 | N/A | 29.83 | 56000 | 1400 | N/A | 38.45 | 23300 | 689 |
| | 32 | 30.93 | | | N/A | 29.95 | | | N/A | 39.58 | | |
| | 31.1 | 29.37 | | | N/A | 29.67 | | | N/A | 41.28 | | |
| $10^{-6}$ | 34.8 | 32.70 | 970 | 25 | N/A | 32.44 | 5600 | 140 | N/A | 43.98 | 2330 | 68.9 |
| | 33.3 | 33.13 | | | N/A | 32.43 | | | N/A | 43.63 | | |
| | 33.5 | 32.50 | | | N/A | 32.02 | | | N/A | N/A | | |
| $10^{-7}$ | 38.4 | 35.57 | 97 | 2.5 | N/A | 34.71 | 560 | 14 | N/A | N/A | 233 | 6.9 |
| | 36 | 35.33 | | | N/A | 35.53 | | | N/A | N/A | | |
| | 38.9 | 35.91 | | | N/A | 35.33 | | | N/A | N/A | | |
| $10^{-8}$ | 41.2 | 38.89 | 9.7 | 0.25 | N/A | 37.82 | 56 | 1.4 | N/A | N/A | 23.3 | 0.7 |
| | 41.9 | 37.78 | | | N/A | 39.48 | | | N/A | N/A | | |
| | 43.6 | N/A | | | N/A | 37.60 | | | N/A | N/A | | |

| | Strain | | | | | | | | | | |
|---|---|---|---|---|---|---|---|---|---|---|---|
| | S. houtanae CIP 82.32 (group IV) | | | | S. bangori CIP 82.33 (group V) | | | S. indica CIP 102501 (group VI) | | | |
| Dilution | Ct with Set 1 | Ct with Set 3 | cfu/ mL | cfu/ PCR | Ct with Set 1 | Ct with Set 3 | cfu/ PCR | Ct with Set 1 | Ct with Set 3 | cfu/ mL | cfu/ PCR |
| $10^{-5}$ | N/A | 32.71 | 24700 | 603 | N/A | 31.41 | 25700 | 892 | N/A | 29.13 | 20300 | 545 |
| | N/A | 33.35 | | | N/A | 32.44 | | | N/A | 28.66 | | |
| | N/A | 32.56 | | | N/A | 31.42 | | | N/A | 28.74 | | |
| $10^{-6}$ | N/A | 35.33 | 2470 | 60.3 | N/A | 34.06 | 2570 | 89.2 | N/A | 32.10 | 2030 | 54.5 |
| | N/A | 34.97 | | | N/A | 34.89 | | | N/A | 32.21 | | |
| | N/A | 35.13 | | | N/A | 34.52 | | | N/A | 32.14 | | |
| $10^{-7}$ | N/A | 38.33 | 247 | 6.0 | N/A | 36.90 | 257 | 8.9 | N/A | 35.47 | 203 | 5.4 |
| | N/A | 37.85 | | | N/A | 37.31 | | | N/A | 35.65 | | |
| | N/A | 37.29 | | | N/A | 37.00 | | | N/A | 35.45 | | |

TABLE 5-continued

| $10^{-8}$ | N/A | 44.25 | 24.7 | 0.6 | N/A | 39.85 | 25.7 | 0.9 | N/A | 42.10 | 20.3 | 0.5 |
| --- | --- | --- | --- | --- | --- | --- | --- | --- | --- | --- | --- | --- |
|  | N/A | 41.49 |  |  | N/A | 43.21 |  |  | N/A | 40.57 |  |  |
|  | N/A | 40.20 |  |  | N/A | 42.01 |  |  | N/A | N/A |  |  |

In table 5 above:
N/A means NOT DETECTED,
cfu/mL means the number of *Salmonella* cfu per mL, as measured by cell count on cell culture;
cfu/PCR means the theoretical number of *Salmonella* cfu placed in each PCR tube.

At a dilution of $10^{-5}$, oligonucleotide set 1 does not detect *S. diarizonae* CIP 82.31 or *S. indica* CIP 102501 anymore, whereas oligonucleotide set 3 detects them at $10^{-5}$ and $10^{-7}$, respectively.

Down to a dilution of $10^{-7}$, oligonucleotide set 3 gives better CT values on *S. salamae* than set 1. At $10^{-8}$, set 3 gives two CT values that are better than the ones obtained with set 1.

On *S. arizonae* and *S. bongori*, set 3 gives accurate CT values, even at a dilution of $10^{-8}$, whereas set I does not detect these strains at all.

The overall results demonstrate that set 3 is much more sensitive than set 1.

Set 3 further has a very wide group I coverage; it detects all *Salmonella* group I serovars, and notably the following *S. enterica* subsp. *enterica* serovars: *S. Typhimurium, S. Typhi, S. Paratyphi, S. Virchow, S. Hadar, S. Enteritidis, S. Anatum, S. Senftenberg, S. Cerro, S. Poona, S. Grumpensis, S. Dalhem, S. Kentucky, S. Lomita, S. Kirkee, S. Bredeney, S. Carrau, S. Aberdeen, S. Tenessee.*

Conclusions:

Sets 2, 3 and 4, which are oligonucleotide sets of the invention, have a wider *Salmonella* detection range than set 1.

Set 3, as well as set 4, cover the six *Salmonella* reference strains, whereas set 1 covers only three of the six strains.

Set 3 is also much more sensitive than set 1; on average, the gain in sensitivity is of about 2 Log.

Example 2

Comparative Example

Naturally-Contaminated Food Material

Ten samples of milk or fermented milk, which were susceptible of being naturally-contaminated by *Salmonella*, were collected for comparative analysis.

Each milk or fermented milk sample was treated as follows:

25 grams of milk sample were incubated with buffered peptone water at 37° C. for 20 hours. One milliliter of incubated medium was centrifuged to remove the supernatant. The pellet was submitted to DNA extraction with 200 μL of lysis buffer using the InstaGen matrix (Bio-Rad, Hercules, U.S.A.), as above-described in example 1.

Five microliters of extract were used for each *Salmonella* analysis.

Each of the ten extracts was analyzed:
by cell culture, in accordance with the European Standard EN ISO 6579:2002 (International Standard ISO 6579: 2002);
by real-time PCR, using oligonucleotide set 1—which is not a set of the invention—(primers of SEQ ID NO: 1 and 3; probe of SEQ ID NO: 8);
by real-time PCR, using oligonucleotide set 3—which is a set of the invention—(primers of SEQ ID NO: 1, 2, 3 and 4; probe of SEQ ID NO: 6).

Real-time PCR were performed as described in example 1, using set 1 or set 3. Results of the cell culture assays are presence (+) or absence (−) of *Salmonella*. PCR results are illustrated by the measured Ct values.

Illustrative results are as follows:

TABLE 6

| Sample n° | FAM Ct | | Cell culture |
| --- | --- | --- | --- |
|  | set 1 | set 3 |  |
| 1 | N/A | N/A | − |
| 2 | N/A | N/A | − |
| 3 | 39.33 | 32.83 | + |
| 4 | N/A | 38.58 | + |
| 5 | 47.44 | 38.07 | + |
| 6 | N/A | N/A | − |
| 7 | N/A | N/A | − |
| 8 | N/A | N/A | − |
| 9 | 19.28 | 21.25 | + |
| 10 | 38.65 | 33.02 | + |

N/A means not detected.

Samples n°1, 2, 6, 7 and 8 are *Salmonella*-negative in cell culture, as well as by PCR analysis.

Sample n°4 is *Salmonella*-positive in cell culture. Analysis of this sample by PCR using set 1 of oligonucleotides gives a false negative result. Such a false negative result is not obtained using set 3 of the invention.

Using Set 1, samples n°5 and n°10 appear to be only weakly positive samples, whereas the cell culture analysis demonstrates that these samples clearly are *Salmonella*-positive. Compared to set 1, oligonucleotide set 3 of the invention highly improves the detection of these two samples.

Oligonucleotide set 3 enables to detect *Salmonella* serovars that may not be detected using oligonucleotide set 1.

Oligonucleotide set 3 avoids false negative results that are obtained by using set 1.

Example 3

Table 7 below presents 58 strains that were tested with oligonucleotide SET 3 (see examples 1 and 2) for exclusivity study. DNA was extracted from a pure culture of each strain (in the appropriate culture conditions) with InstaGen Matrix, as described in examples 1 and 2. SET3 does not detect any of these strains.

TABLE 7

| Strain | Deposit n° |
| --- | --- |
| *Shigella sonei* | ATCC 25931 |
| *Aeromonas hydrophila* | CIP 76.14 |
| *Aeromonas hydrophila* | CIP 76.15 |
| *Aeromonas hydrophila* | CIP 107500 |
| *Bacillus cereus* | ATCC 11778 |
| *Bacillus sphaericus* | DSMZ 28 |
| *Bacillus subtilis* | ATCC 6633 |
| *Brochothrix campestris* | DSMZ 4712 |

TABLE 7-continued

| Strain | Deposit n° |
| --- | --- |
| Brochothrix thermosphacta | DSMZ 20171 |
| Candida albicans | ATCC10231 |
| Citrobacter freundii | ATCC 8090 |
| Citrobacter freundii | ATCC 8090 |
| Corynebacterium bovis | DSMZ 20582 |
| E. coli | ATCC 25922 |
| E. coli | ATCC 8739 |
| E. coli N° 44 | CIP 105243 |
| E. coli N° 46 | CIP 105245 |
| Enterobacter aerogenes | ATCC 13048 |
| Enterobacter cloacae | ATCC 23355 |
| Enterococcus durans | ATCC 19432 |
| Enterococcus faecium | CIP 54.32 |
| Erysipelothrix rhusiopathiae | DSMZ 5055 |
| Escherichia coli | DSMZ 30083 |
| Hafnia alvei | CIP 57.31 |
| Klebsiella pneumoniae | ATCC 13883 |
| Kurtia sibirica | DSMZ 4747 |
| Kurtia gibsonii | DSMZ 20636 |
| Lactobacillus fermentum | ATCC 9338 |
| Lactobacillus plantarum | ATCC 8014 |
| Listeria grayi | CLIP 73019 |
| Listeria innocua | CLIP 74915 |
| Listeria ivanovii | CLIP 12229 |
| Listeria ivanovii | CLIP 74914 |
| Listeria mono 1/2a | CLIP 74902 |
| Legionella hackeliae | ATCC 35999 |
| Legionella wadworthi | ATCC 33877 |
| Listeria mono 1/2b | CLIP 74903 |
| Listeria mono 3a | CLIP 74905 |
| Listeria mono 4a | CLIP 74908 |
| Listeria mono 4b | ATCC 19115 |
| Listeria seeligeri | CLIP 3021 |
| Listeria welshimeri | CLIP 73020 |
| Myroïdes adoratus | CIP 105170 |
| Myroïdes adoratus | CIP 103105 |
| Proteus mirabilis | ATCC 25933 |
| Proteus hauseri | ATCC 13315 |
| Pseudomonas aeruginosa | ATCC 25619 |
| Pseudomonas aeruginosa | ATCC 27853 |
| Serratia marcescens | ATCC 8100 |
| Serratia marcescens N° 20 | CIP 103235 |
| Serratia marcescens N° 21 | CIP 53.86 |
| Serratia marcescens N° 22 | CIP 53100 |
| Shigella flexneri | ATCC 12022 |
| Staphylococcus aureus | ATCC 25923 |
| Staphylococcus aureus | ATCC 44555 |
| Staphylococcus aureus | ATCC 53840 |
| Staphylococcus aureus | ATCC 6538 |
| Staphylococcus epidermidis | ATCC 14990 |

Oligonucleotide set 3 has an excellent specificity.

The invention claimed is:

1. A set of oligonucleotides, which comprises:
an oligonucleotide, the sequence of which consists of SEQ ID NO: 2,
an oligonucleotide, the sequence of which consists of SEQ ID NO: 4,
an oligonucleotide, the sequence of which consists of SEQ ID NO: 3, and
an oligonucleotide, the sequence of which consists of SEQ ID NO: 1.

2. The set of claim 1, which further comprises at least one of the following oligonucleotides:
I) an oligonucleotide, the sequence of which consists of SEQ ID NO: 5 or of the complementary sequence thereof, and
II) an oligonucleotide, the sequence of which consists of SEQ ID NO: 5 or of the complementary sequence thereof, which is linked to:
at least one detection label and/or
two complementary adaptor nucleotide sequences of 3 to 10 nucleotides, one of said adaptor sequences being linked at the 5' end of said oligonucleotide of SEQ ID NO: 5 or complementary sequence thereof, the other of said adaptor sequences being linked at the 3' end of said oligonucleotide of SEQ ID NO: 5 or complementary sequence thereof.

3. A set of oligonucleotides, which comprises an oligonucleotide, the sequence of which consists of SEQ ID NO: 4 and at least one of the following oligonucleotides:
I) an oligonucleotide, the sequence of which consists of SEQ ID NO: 2,
II) an oligonucleotide, the sequence of which consists of SEQ ID NO: 5 or of the complementary sequence thereof,
III) an oligonucleotide, the sequence of which consists of SEQ ID NO: 5 or of the complementary sequence thereof, which is linked to:
at least one detection label and/or
to two complementary adaptor nucleotide sequences of 3 to 10 nucleotides, one of said adaptor sequences being linked at the 5' end of said oligonucleotide of SEQ ID NO: 5 or complementary sequence thereof, the other of said adaptor sequences being linked at the 3' end of said oligonucleotide of SEQ ID NO: 5 or complementary sequence thereof, IV) an oligonucleotide, the sequence of which consists of SEQ ID NO: 3, and V) an oligonucleotide, the sequence of which consists of SEQ ID NO: 1.

4. A set of oligonucleotides, which comprises an oligonucleotide, the sequence of which consists of SEQ ID NO: 4, an oligonucleotide, the sequence of which consists of SEQ ID NO: 2 and at least one of the following oligonucleotides:

I) an oligonucleotide, the sequence of which consists of SEQ ID NO: 5 or of the complementary sequence thereof, and II) an oligonucleotide, the sequence of which consists of SEQ ID NO: 5 or of the complementary sequence thereof, which is linked to:
at least one detection label and/or
two complementary adaptor nucleotide sequences of 3 to 10 nucleotides, one of said adaptor sequences being linked at the 5' end of said oligonucleotide of SEQ ID NO: 5 or complementary sequence thereof, the other of said adaptor sequences being linked at the 3' end of said oligonucleotide of SEQ ID NO: 5 or complementary sequence thereof.

5. A set of oligonucleotides, which comprises an oligonucleotide, the sequence of which consists of SEQ ID NO: 4 and an oligonucleotide, the sequence of which consists of SEQ ID NO: 2.

6. A set of oligonucleotides, which comprises an oligonucleotide, the sequence of which consists of SEQ ID NO: 4 and at least one of the following oligonucleotides:

I) an oligonucleotide, the sequence of which consists of SEQ ID NO: 2,

II) an oligonucleotide, the sequence of which consists of SEQ ID NO: 5 or of the complementary sequence thereof, and III) an oligonucleotide, the sequence of which consists of SEQ ID NO: 5 or of the complementary sequence thereof, which is linked to:
at least one detection label and/or
two complementary adaptor nucleotide sequences of 3 to 10 nucleotides, one of said adaptor sequences being linked at the 5' end of said oligonucleotide of SEQ ID NO: 5, the other of said adaptor sequences being linked at the 3' end of said oligonucleotide of SEQ ID NO: 5.

7. The set of any one of claims 4, 5 and 6, which further comprises at least one oligonucleotide selected from the group consisting of a sequence which consists of SEQ ID NO: 1 and a sequence which consists of SEQ ID NO: 3.

8. The set of any one of claims 3, 4, 2 and 6 which comprises the oligonucleotide, the sequence of which consists of SEQ ID NO: 5, or of the complementary oligonucleotide thereof.

9. The set of any one claims 3, 4, 2 and 6, wherein the sequence of said two complementary adaptor nucleotide sequences of 3 to 10 nucleotides consist of CGCGAC and GTCGCG, respectively.

10. An amplification mix, which comprises:
at least one set of oligonucleotides of any one of claims 1, 3, 4, 2, 5 and 6.

11. A kit, which comprises:
at least one set of oligonucleotides of any one of claims 1, 3, 4, 2, 5 and 6.

12. The kit of claim 11, which further comprises at least one among the following elements:
at least one nucleic acid extraction solution,
at least one DNA polymerase,
at least one dNTP,
at least one buffer having a pH adapted to the polymerase activity of said at least one DNA polymerase,
at least one instruction leaflet advising of performing a real-time multiplex amplification, to detect *Salmonella*, buffered peptone water.

13. A process for the detection of *Salmonella* in a sample, which comprises:
optionally, homogenizing said sample,
optionally, incubating said sample, or said homogenized sample, in buffered peptone water for 18±2 hours,
optionally, extracting the nucleic acids from said sample, or from said homogenized sample, or from the pellet recovered by centrifugation of said peptone-incubated sample,
submitting said sample or homogenized sample or pellet, or a nucleic acid extract thereof, to nucleic acid amplification using the four oligonucleotides contained in the set of claim 1, as primers,
detecting whether an amplicon has been, or is, produced by said nucleic acid amplification,
whereby a positive detection is indicative of the fact that at least one *Salmonella* is present in said sample.

14. The process of claim 13, wherein said sample or said homogenized sample is not incubated in buffered peptone water for 18±2 hours.

15. The process of claim 13, wherein said amplicon detection comprises using as a probe the oligonucleotide, the sequence of which consists of SEQ ID NO: 5, or of the complementary oligonucleotide thereof.

16. The process of claim 15, wherein said amplicon detection further comprises using at least one other oligonucleotide, which is specific of one or several Salmonella strain(s) and/or serovar(s) and/or subspecies and/or species, as a probe.

17. The process of claim 13, which is a real-time amplification process.

18. A process to check the safety of products that are intended for human and/or animal consumption, or the safety of a food and/or beverage product, or of a product that is used in the manufacture of a food and/or beverage product, which comprises the detection of *Salmonella*, wherein said detection of *Salmonella* is made by the process of claim 13.

* * * * *

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial
<220> FEATURE:
<223> OTHER INFORMATION: Salmonella forward primer

<400> SEQUENCE: 1
cacgcaggaa ataacaggac tt                                          22

<210> SEQ ID NO 2
<211> LENGTH: 22
<212> TYPE: DNA
<213> ORGANISM: Artificial
<220> FEATURE:
<223> OTHER INFORMATION: Salmonella forward primer

<400> SEQUENCE: 2
caagcatgaa ataacagggc tt                                          22

<210> SEQ ID NO 3
<211> LENGTH: 17
<212> TYPE: DNA
<213> ORGANISM: Artificial
<220> FEATURE:
<223> OTHER INFORMATION: Salmonella reverse primer

<400> SEQUENCE: 3
gggcaaccag cactaac                                                17

<210> SEQ ID NO 4
<211> LENGTH: 19
<212> TYPE: DNA
<213> ORGANISM: Artificial
<220> FEATURE:
<223> OTHER INFORMATION: Salmonella reverse primer
```

```
-continued

<400> SEQUENCE: 4
gagcaaccag tactaatgg                                                    19

<210> SEQ ID NO 5
<211> LENGTH: 25
<212> TYPE: DNA
<213> ORGANISM: Artificial
<220> FEATURE:
<223> OTHER INFORMATION: Salmonella probe

<400> SEQUENCE: 5
tgtcagaata gtgagcgtgc cttac                                             25

<210> SEQ ID NO 6
<211> LENGTH: 37
<212> TYPE: DNA
<213> ORGANISM: Artificial
<220> FEATURE:
<223> OTHER INFORMATION: Salmonella beacon probe

<400> SEQUENCE: 6
cgcgactgtc agaatagtga gcgtgcctta cgtcgcg                                37

<210> SEQ ID NO 7
<211> LENGTH: 24
<212> TYPE: DNA
<213> ORGANISM: Artificial
<220> FEATURE:
<223> OTHER INFORMATION: Salmonella probe

<400> SEQUENCE: 7
aatagtgagc gtgccttacc gacg                                              24

<210> SEQ ID NO 8
<211> LENGTH: 36
<212> TYPE: DNA
<213> ORGANISM: Artificial
<220> FEATURE:
<223> OTHER INFORMATION: Salmonella beacon probe

<400> SEQUENCE: 8
cgcagcaata gtgagcgtgc cttaccgacg gctgcg                                 36
```